(12) United States Patent
DeRosa et al.

(10) Patent No.: US 12,265,075 B2
(45) Date of Patent: Apr. 1, 2025

(54) METHODS AND APPARATUSES FOR MONITORING THE CURING OF A PHOTOCURABLE MATERIAL

(71) Applicant: CORNING INCORPORATED, Corning, NY (US)

(72) Inventors: Michael Edward DeRosa, Painted Post, NY (US); Stephan Lvovich Logunov, Corning, NY (US)

(73) Assignee: Corning Incorporated, Corning, NY (US)

(*) Notice: Subject to any disclaimer, the term of this patent is extended or adjusted under 35 U.S.C. 154(b) by 919 days.

(21) Appl. No.: 17/215,499

(22) Filed: Mar. 29, 2021

(65) Prior Publication Data

US 2021/0333260 A1 Oct. 28, 2021

Related U.S. Application Data

(60) Provisional application No. 63/015,047, filed on Apr. 24, 2020.

(51) Int. Cl.
*C08J 3/28* (2006.01)
*G01N 21/41* (2006.01)
*G01N 21/55* (2014.01)
*G01N 33/44* (2006.01)

(52) U.S. Cl.
CPC .............. *G01N 33/442* (2013.01); *C08J 3/28* (2013.01); *G01N 21/412* (2013.01); *G01N 21/55* (2013.01); *G01N 2021/551* (2013.01); *G01N 2201/0694* (2013.01); *G01N 2201/08* (2013.01); *G01N 2201/126* (2013.01)

(58) Field of Classification Search
CPC .... G01N 33/442; G01N 21/412; G01N 21/55; G01N 2021/551; G01N 2201/0694; G01N 2201/08; G01N 2201/126; C08J 3/28
See application file for complete search history.

(56) References Cited

U.S. PATENT DOCUMENTS

| | | | | |
|---|---|---|---|---|
| 4,465,335 A | * | 8/1984 | Eppes | G02B 6/2804 |
| | | | | 385/127 |
| 4,904,080 A | | 2/1990 | Afromowitz | |
| 7,091,254 B2 | * | 8/2006 | Crivello | G01J 5/0003 |
| | | | | 522/170 |

(Continued)

FOREIGN PATENT DOCUMENTS

CN 1148170 A * 4/1997

OTHER PUBLICATIONS

Wikipedia "Optical Fiber" (Year: 2020).*

(Continued)

*Primary Examiner* — Jill A Warden
*Assistant Examiner* — Michael Stanley Gzybowski
(74) *Attorney, Agent, or Firm* — Kevin L. Bray

(57) ABSTRACT

Apparatuses and methods for monitoring curing of photocurable material are disclosed. The methods generally include directing an ultraviolet cure light into a photocurable material, wherein the ultraviolet cure light causes the photocurable material to cure; directing a probe light into the photocurable material through an optical fiber during the cure; collecting a back reflection signal from the photocurable material with the optical fiber; and determining a refractive index change of the photocurable material during the cure.

12 Claims, 7 Drawing Sheets

(56) References Cited

U.S. PATENT DOCUMENTS

| | | | | |
|---|---|---|---|---|
| 8,946,637 B2* | 2/2015 | Chinn | ............... | G01S 7/4817 |
| | | | | 250/338.4 |
| 2004/0131320 A1* | 7/2004 | Inui | ............... | C08J 3/28 |
| | | | | 385/123 |
| 2009/0263091 A1* | 10/2009 | Kumano | ............ | G02B 6/02019 |
| | | | | 385/127 |

OTHER PUBLICATIONS

Wikipedia "Refractive Index" (Year: 2020).*
Cusano et al., "Optoelectronic refractive Index Measurements: Application to smart processing", IEEE Sensors Journal, vol. 3, No. 6, 2003, pp. 781-787.
Derosa et al., "Photothermal behavior of and optical path adhesive for photonics applications at 1550 nm", Applied Optics, vol. 40, No. 36, Dec. 2001, 6611-6617.
Kosaka et al., "Cure monitoring of UV chain curing polymer by fiber optic measurement of refractive index", Proceedings of the 16th International Conference on Composite Materials, 2007 pp. 1-8.
Peng et al. "Novel optical fiber sensor system for the real-time monitoring of light curing process", Journal 2009, vol. 20, Issue 4, pp. 4 (1 page of English Abstract and 3 pages of Original Document).

* cited by examiner

METHODS AND APPARATUSES FOR MONITORING THE CURING OF A PHOTOCURABLE MATERIAL

This application claims the benefit of priority from U.S. Provisional Patent Application Ser. No. 63/015,047 filed on Apr. 24, 2020, the content of which is relied upon and incorporated herein by reference in its entirety.

TECHNICAL FIELD

The present disclosure generally relates to methods for determining the cure kinetics of photocurable materials. More particularly, the present disclosure relates to methods for using back-reflectance to determine the cure kinetics of photocurable materials.

BACKGROUND

Conventional methods for measuring photopolymerization cure kinetics may include Fourier-transform infrared spectroscopy (FTIR), photo-differential scanning calorimetry (photo-DSC), and oscillatory shear rheology methods. FTIR methods monitor the chemical kinetics of the polymer by measuring the disappearance of the acrylate groups of photocurable acrylate polymers during cure. Photo-DSC methods monitor cure kinetics by measuring the amount of heat generated during the exothermic cure reaction. Rheological methods monitor cure kinetics by measuring the mechanical properties of the photocurable material as the network builds in size and molecular weight during cure.

However, each method has limitations that affect the rate at which the data points may be collected while the photocurable material cures ("data collection rate"). For example, the data collection rate of FTIR methods may be limited by the wavenumber resolution and scan time over the peaks of interest, and the data collection rate of rheology methods may be limited by the mechanical frequency used. Additionally, ultraviolet cure light intensities limit any current methods that may have a relatively low data collection rate (i.e. a rate that collects each data point in less than 35 milliseconds (ms)), preventing these current methods from collecting sufficient cure kinetics data.

Accordingly, a need exists for alternative methods of measuring the cure kinetics of photocurable materials, such as ultraviolet-curable acrylates, which may have relatively high rates of reaction. More specifically, a need exists for methods that have the ability to collect cure kinetics data for a photocurable materials under manufacturing conditions, such as under draw conditions in the case of photocurable materials applied to optical fiber, which include ultraviolet light intensities greater than at least 1 W/cm$^2$, coupled with a data collection rate that has the ability to collect each data point in less than at least 35 milliseconds (ms).

SUMMARY

Embodiments herein address these needs by monitoring the change in refractive index of a photocurable material at the interface between the photocurable material and a substrate, which is referred to as "back reflectance."

According to a first aspect, a method of monitoring curing of a photocurable material is provided. The method may include directing an ultraviolet cure light into a photocurable material, wherein the ultraviolet cure light causes the photocurable material to cure; directing a probe light into the photocurable material through an optical fiber during the cure; collecting a back reflection signal from the photocurable material with the optical fiber; and determining a refractive index change of the photocurable material during the cure.

A second aspect may include the first aspect, further comprising determining the refractive index change of the photocurable material during cure as a function of time.

A third aspect may include any preceding aspect, further comprising aligning the probe light and the ultraviolet cure light.

A fourth aspect may include any preceding aspect, wherein the optical fiber is a concentric core optical fiber.

A fifth aspect may include any preceding aspect, wherein the ultraviolet cure light has an intensity of from greater than or equal to 0.1 W/cm$^2$ to less than or equal to 700 W/cm$^2$.

A sixth aspect may include any preceding aspect, wherein collecting the back reflection signal occurs at a data collection rate of less than 35 milliseconds (ms) per data point.

A seventh aspect may include any preceding aspect, wherein collecting the back reflection signal occurs at a data collection rate of less than 100 microseconds (µs) per data point.

According to an eighth aspect, a method of monitoring curing of a photocurable material is provided. The method may include directing an ultraviolet cure light into a photocurable material, wherein the ultraviolet cure light causes the photocurable material to cure; directing a probe light into the photocurable material through an optical fiber during the cure; collecting a signal from the photocurable material with the optical fiber at a data collection rate of less than 35 milliseconds (ms) per data point; and determining a refractive index change of the photocurable material during the cure.

A ninth aspect may include the eighth aspect, further comprising determining the refractive index change of the photocurable material during cure as a function of time.

A tenth aspect may include any of the eighth through ninth aspects, wherein the optical fiber is a concentric core optical fiber.

An eleventh aspect may include any of the eighth through tenth aspects, wherein the ultraviolet cure light has an intensity of from greater than or equal to 0.1 W/cm$^2$ to less than or equal to 700 W/cm$^2$.

A twelfth aspect may include any of the eighth through eleventh aspects, wherein collecting the back reflection signal occurs at a data collection rate of from 1 microseconds (µs) to 2 µs per data point.

According to a thirteenth aspect, an apparatus for monitoring curing of a photocurable material is provided. The apparatus may include an ultraviolet cure light for curing the photocurable material; an optical fiber having a terminal end and a coupling end; a probe light source optically coupled to the coupling end of the optical fiber such that the optical fiber emits a probe light from the terminal end and into the photocurable material; a detector optically coupled to the coupling end of the optical fiber; and a control unit communicatively coupled to the detector. The control unit may include a processor, and a memory storing logic comprising computer readable and executable instructions, which, when executed by the processor, cause the processor to receive a detector signal, from the detector, indicative of the back reflectance of the probe light directed into the photocurable material through the optical fiber as the photocurable material is cured with the ultraviolet cure light; and determine a refractive index change of the photocurable material as the photocurable material is cured based on the detector signal.

A fourteenth aspect may include the thirteenth aspect, wherein the ultraviolet cure light has an intensity of greater than or equal to 0.1 W/cm².

A fifteenth aspect may include the thirteenth aspect, wherein the ultraviolet cure light has an intensity of from greater than or equal to 0.1 W/cm² to less than or equal to 700 W/cm².

A sixteenth aspect may include any of the thirteenth through fifteenth aspects, wherein the optical fiber is a concentric core optical fiber comprising a terminal end, a coupling end, an inner core, and an outer core in direct contact with and at least partially surrounding the inner core; the ultraviolet cure light is optically coupled the outer core at the coupling end of the concentric core optical fiber; and the probe light source optically coupled to the inner core at the coupling end of the concentric core optical fiber.

A seventeenth aspect may include the sixteenth aspect, wherein the inner core comprises the probe light and a first silica-based glass having a first refractive index; the outer core comprises the ultraviolet cure light and a second silica-based glass having a second refractive index, and the concentric core optical fiber further comprises a cladding in direct contact with and at least partially surrounding and the outer core.

An eighteenth aspect may include any of the sixteenth through seventeenth aspects, wherein the inner core has a diameter greater than or equal to 5 micrometers (μm) to less than or equal to 8 μm, and the outer core has a diameter of from 20 μm to 100 μm.

A nineteenth aspect may include any of the sixteenth through eighteenth aspects, wherein the relative refractive index ($\Delta_1$) between the inner core and the outer core is from greater than or equal to 0.20 to 0.40.

A twentieth aspect may include any of the sixteenth through nineteenth aspects, wherein the relative refractive index ($\Delta_2$) between the outer core and the cladding is from greater than or equal to 0.75 to 1.25.

According to a twenty-first aspect, a method of detecting cure of a photocurable material is provided. The method may include directing cure light to a photocurable material, wherein the cure light causes the photocurable material to cure; directing probe light to the photocurable material, the probe light interacting with the photocurable material to produce a back reflection signal, the back reflection signal comprising Fresnel reflection; detecting the back reflection signal; determining a refractive index of the photocurable material from the back reflection signal; and determining a degree of cure of the photocurable material from the refractive index.

A twenty-second aspect may include the twenty-first aspect, wherein the cure light is provided by a light emitting diode (LED) or a laser diode (LD).

A twenty-third aspect may include the twenty-first aspect, wherein the cure light is an ultraviolet cure light.

A twenty-fourth aspect may include the twenty-first aspect, wherein the probe light has a wavelength longer than the cure light.

A twenty-fifth aspect may include the twenty-first aspect, wherein the cure light has an intensity greater than 0.1 W/cm².

A twenty-sixth aspect may include the twenty-first aspect, wherein the cure light is directed to the photocurable material through an optical fiber, the optical fiber including a coupling end for receiving the cure light and a terminal end, the terminal end directly contacting the photocurable material, the cure light exiting the optical fiber at the terminal end.

A twenty-second aspect may include the twenty-sixth aspect, wherein the probe light is directed to the photocurable material through the terminal end of the optical fiber.

A twenty-eighth aspect may include the twenty-seventh aspect, wherein the optical fiber includes an inner core, an outer core, and a cladding surrounding the inner core and the outer core wherein the inner core and the outer core are concentric; the outer core surrounding the inner core and having a refractive index lower than a refractive index of the inner core and greater than a refractive index of the cladding, the cure light being directed to the photocurable material through the outer core and the probe light being directed to the photocurable material through the inner core.

A twenty-ninth aspect may include the twenty-sixth aspect, wherein the back reflection signal is directed through the optical fiber, the back reflection signal entering the optical fiber at the terminal end.

A thirtieth aspect may include the twenty-first aspect, further comprising determining a refractive index of the photocurable material from the back reflection signal.

A thirty-first aspect may include the thirtieth aspect, further comprising determining a degree of cure of the photocurable material from the refractive index.

A thirty-second aspect may include the thirty-first aspect, wherein the detecting back reflection signal comprises detecting the back reflection signal at a plurality of times spaced apart by a time interval, the time interval being less than 20 ms.

A thirty-third aspect may include the thirty-second aspect, wherein the time interval is less than 1 ms.

A thirty-fourth aspect may include the thirty-second aspect, wherein the time interval is less than 100 μs.

A thirty-fifth aspect may include the thirty-second aspect, wherein the time interval is less than 10 μs.

Additional features and advantages of the compositions, methods, and articles described herein will be set forth in the detailed description that follows, and in part will be readily apparent to those skilled in the art from that description or recognized by practicing the embodiments described herein, including the detailed description that follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
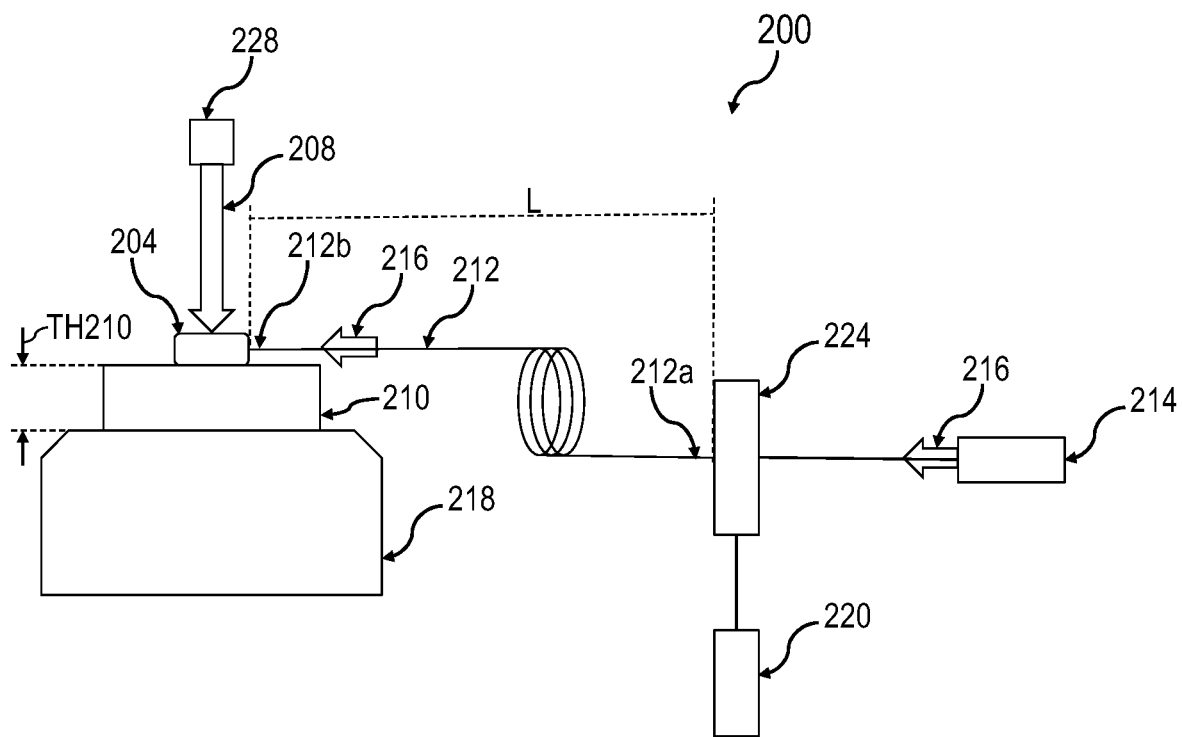
FIG. 1 schematically depicts an apparatus for monitoring the cure kinetics of photocurable material, according to embodiments.

The following description of the embodiments is illustrative in nature and is in no way intended to be limiting in its application or use. Furthermore, it should be understood that like reference numbers indicate corresponding or related parts in the various figures.

As used herein, the singular forms "a," "an," and "the" include plural referents unless the context clearly dictates otherwise. Thus, for example, reference to "a" component includes aspects having one such component as well as aspects having two or more such components, unless the context clearly indicates otherwise.

Directional terms as used herein—for example up, down, right, left, front, back, top, bottom, above, below—are made only with reference to the figures as drawn and are not intended to imply absolute orientation unless otherwise specified.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation; and the number or type of embodiments described in the specification.

As used herein, a "photocurable material," is a material that undergoes a chemical reaction when exposed to light, for example, in the ultraviolet or visible region of the electromagnetic spectrum. In embodiments, the photocurable material may include an ethylenically unsaturated group and the chemical reaction is a reaction of the ethylenically unsaturated group. In embodiments, reaction of the ethylenically unsaturated group is a polymerization reaction, such as a free radical polymerization reaction. Examples of ethylenically unsaturated groups include acrylate groups and methacrylate groups. Products formed by the chemical reaction include acrylate oligomers and polymers and methacrylate oligomers and polymers. In a preferred embodiment, the photocurable material reacts to form a product suitable for use as a coating on an optical fiber.

As used herein, the term "back reflectance" means light reflected from a surface of a photocurable material. In one embodiment, back reflection refers to light reflected from an interface between a photocurable material and an optical fiber.

As used herein, the "refractive index profile," refers to the relationship between refractive index or relative refractive index and the radius of the optical fiber.

As used herein, the term "refractive index difference" refers to the difference between the refractive index of a core of the optical fiber and the refractive index of the material (e.g. photocurable material or reaction product of a photocurable material) next to the tip of a distal end of the optical fiber, where the optical fiber is cleaved at 90 degrees (+/−1 degree) relative to the central axis of the optical fiber.

As used herein, the term "ultraviolet" refers to light having a wavelength of 400 nm or less.

Methods for monitoring the cure kinetics of photocurable materials may be relevant to a variety of applications, such as for primary and secondary optical fiber coatings applications. However, conventional methods may have limitations that prevent the collection of a sufficient amount of data when photocurable materials are tested under draw-like or manufacturing conditions.

As stated herein, conventional measurement methods for photopolymerization cure kinetics include Fourier-transform infrared spectroscopy (FTIR), photo-differential scanning calorimetry (photo-DSC), and oscillatory shear rheology methods. FTIR methods monitor the chemical kinetics of the polymer by measuring the disappearance of the acrylate groups of photocurable acrylate polymers during cure. Photo-DSC methods monitor cure kinetics by measuring the amount of heat generated during the exothermic cure reaction. Rheological methods monitor cure kinetics by measuring the mechanical properties of the photocurable material as the network builds in size and molecular weight during cure.

However, these methods have limitations. For example, FTIR methods may typically be limited to 35 milliseconds (ms) per data point due to resolution and scanning time limitations of the measurement technique. Also, rheology methods may be limited by the mechanical frequency available from the measurement technique. For example, the maximum data collection rate of such rheology methods may typically be twice the mechanical frequency (typically about 25 Hz), which would result in 20 ms per data point. The long sampling times between data points limits the ability of these techniques to adequately determine the cure kinetics of materials that undergo rapid chemical reactions.

Because of these rate limitations, conventional methods may be further limited by the intensity of the cure light that can be used to conduct measurements of curing kinetics. For example, when an optical fiber coating material is exposed to ultraviolet cure light at the high intensities consistent with fiber draw conditions used in practical manufacturing, the coating material may have a rate of reaction that is too high to measure accurately with conventional methods. Therefore, when used with photocurable materials having rapid reaction rates, conventional methods, such as FTIR and rheology, are limited to ultraviolet cure light intensities of less than about 0.1 W/cm² to so that a sufficient number of data points can be collected to accurately determine cure kinetics. However, on a manufacturing-scale draw tower, photocurable coatings may be exposed to intensities on the order of 10 W/cm² to 30 W/cm², which are at least about 100 times higher than the maximum ultraviolet light intensities available from FTIR and rheology methods for typical photocurable optical fiber coating materials.

Accordingly, needs exist for alternative methods for determining the cure kinetics of photocurable materials, such as ultraviolet-curable acrylates, which may have relatively high rates of reaction under preferred reaction conditions. More specifically, needs exist for methods that have the ability to obtain information about cure kinetics of photocurable materials under draw-like conditions, such as at manufacturing conditions, including curing photocurable optical fiber coating materials with ultraviolet cure light intensities greater than at least 0.1 W/cm², coupled with a data collection rate that has the ability to collect each data point in less than at least 35 milliseconds (ms). Shorter time intervals between data points improves the accuracy of kinetic analysis of rapidly reacting photocurable materials.

As will be described in more detail herein, the disclosed methods may allow for cure kinetics data to be collected at conditions similar those of a draw tower. More specifically, the embodiments described herein may be directed to lab-scale methods of measuring the cure kinetics of photocurable materials that simulate manufacturing-scale conditions for optical fibers, such as utilizing ultraviolet cure light intensities greater than at least 0.1 W/cm². Even at manufacturing-scale conditions, the methods disclosed herein may provide data collection rate that has the ability to collect each data point in less than at least 35 milliseconds (ms).

As will be described in more detail subsequently in this disclosure, the present apparatuses and methods may include a single-mode optical fiber having a flat, cleaved terminal end. This optical fiber may act as a probe embedded in a photocurable material to be analyzed. In other embodiments, a multi-mode optical fiber may be utilized.

The methods described herein utilize back reflectance techniques to monitor the cure kinetics of the photocurable material. As the photocurable material cures, its density may increase. This increase in density may therefore result in an increase in the refractive index of the photocurable material. Therefore, as the photocurable material cures (for example, as a result of exposure to ultraviolet light) there may be a difference in refractive index between the photocurable material and a core of the optical fiber. Any interface where the index of refraction differs causes light to be reflected, which is known as "Fresnel reflection." The difference in refractive index between the photocurable material and the core of the optical fiber results in a Fresnel reflection, which may be detected back down the optical fiber and subsequently measured. In embodiments, at isothermal or near-isothermal conditions, the reflected probe signal detected due to the refractive index difference may be monitored as a function of time at data rates of less than 35 ms/data point, or less than 10 ms/data point, or less than 1 ms/data point, or less than 500 μs/data point, or less than 250 μs/data point, or less than 100 μs/data point, or less than 50 μs/data point, or less than 25 μs/data point, or less than 10 μs/data point, or less than 1 μs/data point. Accordingly, the refractive index difference as a function of time may then be correlated to the degree of cure for the photocurable material.

In embodiments, the method of monitoring the curing of a photocurable material may include directing an ultraviolet light into a photocurable material, wherein the ultraviolet light causes the photocurable material to cure; directing a probe light into the photocurable material through an optical fiber during the cure; collecting a back reflection signal (probe signal) of the probe light from the interface of the photocurable material with the optical fiber; and determining a refractive index change of the photocurable material during the cure from the back reflection signal.

The method may further include determining refractive index change of the photocurable material during cure as a function of time, as will be described subsequently in more detail. The refractive index change may be correlated with the degree of cure of the photocurable material, which is a measure of the extent to which the curing reaction of the photocurable material proceeds to completion. Prior to directing the ultraviolet light into a photocurable material, the method may further include aligning the probe light and the ultraviolet cure light. As used herein, "aligned" means that the ultraviolet cure light projects onto a larger surface area of the photocurable material than the surface area projected onto by the probe light, and the surface area projected onto by the ultraviolet light overlaps the surface area projected onto by the probe light.

Reference will now be made in detail to various methods and apparatuses for monitoring the curing of a photocurable material which include collecting a back reflection signal from a photocurable material with an optical fiber to determine a refractive index change of the photocurable material during cure. As stated previously, the disclosed methods may provide a non-expensive lab-scale setup which may be capable of reproducing industrial conditions unlike conventional methods of monitoring photopolymerization cure kinetics. As such, the methods described herein may allow for the cure rates to be predicted for various photocurable material compositions under different draw conditions. Draw conditions that may be modified include lamp intensity, wavelength, dark cure time, draw speed, and temperature.

As described herein, the present apparatuses and methods may be utilized to determine the degree of cure for the photocurable material via back reflectance. Generally, the apparatuses may include a probe light, which may be directed into the photocurable material through an optical fiber. As cure light (preferably ultraviolet light) is directed into a photocurable material, the ultraviolet light may cause the photocurable material to cure. As described in more detail subsequently in this disclosure, a probe light may be directed into the photocurable material through the optical fiber. The basic principle of optical back reflectance works by detecting the refractive index change at the end of the optical fiber at the interface between the optical fiber core and the photocurable material. As the photocurable material cures, a back reflection signal may be collected from the photocurable material with the optical fiber.

The difference in the refractive index change between the optical fiber and the photocurable material at its interface with the optical fiber causes a small portion of a probe signal from the probe light to be back reflected as a function of time during cure given. The back reflected probe signal corresponds to a return loss (RL) due to Fresnel reflection. At normal incidence of the probe light at the interface of the optical fiber and photocurable material, the return loss may be calculated according to EQ. 1:

$$RL(t) = -10\log\left(\frac{n_p(t) - n_{fc}}{n_p(t) + n_{fc}}\right)^2 \quad \text{(EQ. 1)}$$

where $n_p(t)$ is the refractive index of the photocurable material at time t and $n_{fc}$ is the refractive index of the core of the optical fiber through which the probe light and back reflection signal propagate.

By rewriting EQ. 1 in linear units, the refractive index of the photocurable material is given by EQ. 2:

$$I(t) = I_0\left(\frac{n_p(t) - n_{fc}}{n_p(t) + n_{fc}}\right)^2 \quad \text{(EQ. 2)}$$

where I(t) is the intensity of the back reflection signal measured by a detector (not pictured), which will be described subsequently in more detail, and where $I_0$ is the incident intensity of the probe light at the interface of the optical fiber with the photocurable material. I(t) and $I_0$ may be measured in Watts (W) microWatts or nanoWatts.

When the change in refractive index of the photocurable material due to curing is small relative to the refractive index of the photocurable material in an uncured state, EQ. 2 can be simplified to EQ. 3:

$$I(t) - I_i \sim 2I_0(n_p(t) - n_0)/(n_0 + n_{fc}) \quad \text{(EQ. 3)}$$

where $I_i$ is an intensity of reflected light from the photocurable material in an uncured state, and $n_0$ is the refractive index of the photocurable material in an uncured state. By relating the refractive index of the photocurable material to its degree of cure, a plot of functional group conversion versus time may be plotted and used as the basis of the kinetics analysis.

FIG. 1 schematically depicts an embodiment of an apparatus 200 for monitoring curing of a photocurable material 204. The apparatus 200 for monitoring curing of photocurable material 204 may include the photocurable material 204, a substrate 210, an optical fiber 212, a probe light 216, a probe light source 214, an ultraviolet cure light 208, an ultraviolet cure light source 228, and a detector 220.

As depicted in FIG. 1, an amount of the photocurable material 204 may be placed on the substrate 210 at the terminal end 212b of the optical fiber 212. In embodiments, the photocurable material 204 may be placed on the terminal end 212b of the optical fiber 212, so that completely covers the terminal end 212b (i.e. the covering both the core and cladding of the optical fiber 212). In some embodiments, a top cover glass plate (not pictured) may be placed on top of the photocurable material 204, which has been be placed on the substrate 210. In embodiments, the amount of the photocurable material 204 that is placed on the terminal end 212b of the optical fiber 212 may be from greater than or equal to 1 microliters (µL) to less than or equal to 3 µL. In embodiments, the amount of the photocurable material 204 that is placed on the terminal end 212b of the optical fiber 212 may be from greater than or equal to 1.0 µL to less than or equal to 3.0 µL, from greater than or equal to 1.0 µL to less than or equal to 2.5 µL, from greater than or equal to 1.0 µL to less than or equal to 2.0 µL, from greater than or equal to 1.0 µL to less than or equal to 1.5 µL, from greater than or equal to 1.5 µL to less than or equal to 3.0 µL, from greater than or equal to 1.5 µL to less than or equal to 2.5 µL, from greater than or equal to 1.5 µL to less than or equal to 2.0 µL, from greater than or equal to 2.0 µL to less than or equal to 3.0 µL, from greater than or equal to 2.0 µL to less than or equal to 2.5 µL, or from greater than or equal to 2.5 µL to less than or equal to 3.0 µL. In embodiments, the optical fiber 212 may be affixed to the substrate 210 by a clip (not pictured) placed on the substrate 210. Alternatively, the optical fiber 212 may be affixed to the substrate 210 with adhesive, mechanical fasteners, or the like.

The substrate includes a body that defines a thickness TH210. Substrate 210 can be made of, for example, glass; plastic; display glass such as Corning's EAGLE XG®, EAGLE®, GORILLA® and PYREX® glasses; as well as fused silica; and plastic materials like polymethyl methacrylate (PMMA) or any other transparent material. Here, the term "transparent" generally means that the substrate transmits probe light 216 at least in the visible wavelength range or near UV range used for polymerization, and transmits more of the probe light 216 than it absorbs for the given thickness TH210 of the substrate 210. In an example, the thickness TH210 of the substrate is 0.3 mm or greater, and in another example the thickness TH210 of the substrate is 0.7 mm or greater. In an example, substrate has a refractive index of 1.5 or greater at 550 nm or even 2.0 or greater at 550 nm. Also in an example, the substrate may have one or more surfaces that may be intentionally textured to scatter the probe light 216.

In embodiments, the substrate 210 may be positioned on a hot stage 218. The hot stage 218 may be utilized to heat the photocurable material 204 to a particular temperature. The hot stage 218 may be heated as the probe light 216 is directed onto the photocurable material 204. In embodiments, the hot stage 218 may be set at a temperature of from greater than or equal to 50 degrees Celsius (° C.) to less than or equal to 130° C. In embodiments, the hot stage 218 may be set at a temperature of from greater than or equal to 50° C. to less than or equal to 100° C., from greater than or equal to 50° C. to less than or equal to 80° C., from greater than or equal to 50° C. to less than or equal to 60° C., from greater than or equal to 60° C. to less than or equal to 130° C., from greater than or equal to 60° C. to less than or equal to 100° C., from greater than or equal to 60° C. to less than or equal to 80° C., from greater than or equal to 80° C. to less than or equal to 130° C., from greater than or equal to 80° C. to less than or equal to 100° C., or from greater than or equal to 100° C. to less than or equal to 130° C. In embodiments, the hot stage 218 may allow for temperature control of the photocurable material 204 to near isothermal conditions. As stated previously, at near isothermal conditions, the back reflectance due to the refractive index change may be monitored as a function of time at data rates less 1 µs per data point and correlated to the degree of cure.

In embodiments, apparatus 200 for monitoring curing of photocurable material 204 includes an optical fiber 212. In an example, optical fiber 212 includes a coupling end 212a and a terminal end 212b. The coupling end 212a and the terminal end 212b define a length L for optical fiber 212. Coupling end 212a is optically coupled to the probe light source 214 via a 2×1 coupler 224 so that the probe light 216 from the probe light source 214 is coupled into the optical fiber 212 as guided light. The terminal end 212b of the optical fiber 212 is disposed above at least one surface of the substrate 210. In embodiments, the terminal end 212b of the optical fiber 212 may be in contact with at least one surface of the substrate 210.

Figure 2:
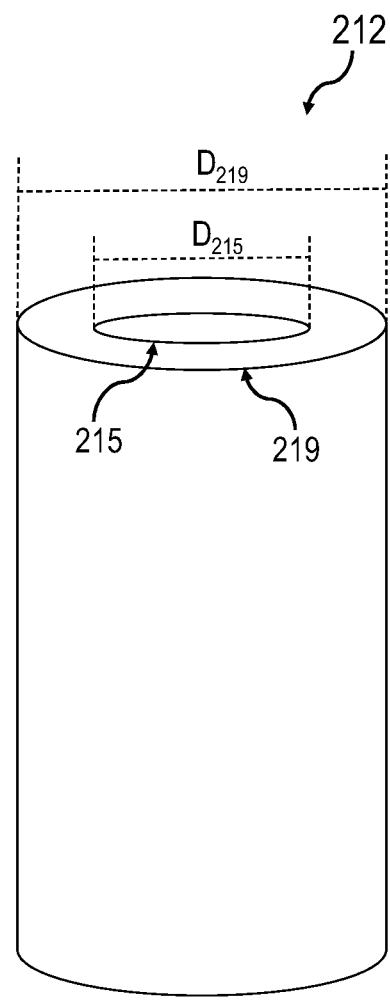
FIG. 2 schematically depicts an embodiment of an optical fiber utilized in the apparatus for monitoring the cure kinetics of photocurable material, according to embodiments.

FIG. 2 schematically depicts an example optical fiber 212 having a core 215, and a cladding 219. The core 215 has a diameter $D_{215}$. The cladding 219 has a diameter $D_{219}$. The refractive index of core 215 is higher than the refractive index of the cladding 219 at the wavelength of the probe light 216. In embodiments, the cladding 219 may at least partially surround the circumference of the core 215. In embodiments, the cladding 219 may entirely surround the circumference of the core 215. In embodiments, the cladding 219 may be made of a low-index polymer. Examples of low index polymers include fluorinated polymers and silicone based polymers. In embodiments, the core 215 may be formed from silica-based glass. However, it should be understood that other embodiments are contemplated and possible, such as embodiments where the core 215 is formed from polymer material.

In embodiments, the core 215 may have a refractive index of greater than or equal to 1.46 at a wavelength of 590 nm. In embodiments, the core 215 may have a refractive index of greater than or equal to 1.46, greater than or equal to 1.50, or greater than or equal to 1.54 at a wavelength of 590 nm. In embodiments, the core 215 may have a refractive index of from greater than or equal to 1.4 to less than or equal to 1.6, from greater than or equal to 1.4 to less than or equal to 1.5, from greater than or equal to 1.5 to less than or equal to 1.6 at a wavelength of 590 nm.

In embodiments, the core 215 may have a diameter $D_{215}$ in the range from greater than or equal to 1 micrometers (microns or μm) to less than or equal to 300 μm. In embodiments, the core may have a diameter $D_{215}$ in the range from greater than or equal to 1 μm to less than or equal to 200 μm, from greater than or equal to 1 μm to less than or equal to 100 μm, from greater than or equal to 1 μm to less than or equal to 50 μm, from greater than or equal to 50 μm to less than or equal to 300 μm, from greater than or equal to 50 μm to less than or equal to 200 μm, from greater than or equal to 50 μm to less than or equal to 100 μm, from greater than or equal to 100 μm to less than or equal to 300 μm, from greater than or equal to 100 μm to less than or equal to 200 μm, or from greater than or equal to 200 μm to less than or equal to 300 μm. In some embodiments, as described in more detail below, the optical fiber 212 may be a single-moded at probe wavelength, and the core 215 may have a diameter $D_{215}$ from greater than or equal to 1 μm to less than or equal to 50 μm, from greater than or equal to 1 μm to less than or equal to 25 μm, or from greater than or equal to 1 μm to less than or equal to 10 μm. In some embodiments, as described in more detail below, the optical fiber 212 may be multi-moded at the wavelength of the probe light 216, and the core 215 may have a diameter $D_{215}$ from greater than or equal to 50 μm to less than or equal to 100 μm or from greater than or equal to 50 μm to less than or equal to 75 μm.

In embodiments, the cladding 219 may have a diameter $D_{219}$ in the range from greater than or equal to 125 micrometers (microns or μm) to less than or equal to 400 μm. In embodiments, the cladding 219 may have a diameter $D_{219}$ in the range from greater than or equal to 200 μm to less than or equal to 350 μm, from greater than or equal to 200 μm to less than or equal to 300 μm, from greater than or equal to 200 μm to less than or equal to 250 μm, from greater than or equal to 250 μm to less than or equal to 400 μm, from greater than or equal to 250 μm to less than or equal to 350 μm, from greater than or equal to 250 μm to less than or equal to 300 μm, from greater than or equal to 300 μm to less than or equal to 400 μm, from greater than or equal to 300 μm to less than or equal to 350 μm, or from greater than or equal to 350 μm to less than or equal to 400 μm.

In embodiments, the optical fiber 212 may further include a coating layer (not shown) that surrounds the cladding 219. In embodiments, the coating layer that surrounds the cladding 219 may be an acrylate polymer material. In further embodiments, the coating layer that surrounds the cladding 219 may be an acrylate polymer material that is different than the photocurable material 204. Exemplary optical fibers may include single-mode fibers, such as SMF-28 Ultra manufactured by Corning Inc., and multimode fibers, such as 50 μm and 62.5 μm multimode fibers manufactured by Corning, Inc.

With reference again to FIG. 1, the optical fiber 212 may emit a probe light 216 originating from the probe light source 214 through the terminal end 212b of the optical fiber 212. The optical fiber 212, specifically the core 215 of the optical fiber, may be optically coupled to the probe light source 214 via a 1×2 coupler 224. In embodiments, the probe light source 214 may include at least one light-emitting diode (LED) or at least one diode laser. In embodiments, the probe light source 214 may be a continuous wave laser. In embodiments, probe light source 214 may include two or more than two LEDs as needed to reach a desired brightness. In embodiments, the LEDs may have dimensions of 1 millimeter (mm)×1 mm. In embodiments, the LEDs may have a power of 1 W.

In embodiments, the probe light source 214 may emit a probe light 216 that is in the wavelength range from greater than or equal to 450 nanometers (nm) to less than or equal to 1,500 nm. In embodiments, the probe light source 214 may emit a probe light 216 that is in the wavelength range from greater than or equal to 450 nm to less than or equal to 1,000 nm, from greater than or equal to 450 nm to less than or equal to 800 nm, from greater than or equal to 450 nm to less than or equal to 600 nm, from greater than or equal to 600 nm to less than or equal to 1,000 nm, from greater than or equal to 600 nm to less than or equal to 800 nm, or from greater than or equal to 800 nm to less than or equal to 1,000 nm.

In embodiments, probe light source 214 may emit a probe light 216 that is in the visible wavelength range, for example, nominally from greater than or equal to 450 nm (blue) nm to less than or equal to 750 nm (red). In further embodiments, the probe light source 214 may emit a probe light 216 that is in the wavelength range from greater than or equal to 450 nm to less than or equal to 600 nm or from greater than or equal to 600 nm to less than or equal to 750 nm. In embodiments, the probe light source 214 may emit probe light 216 at a wavelength of 450 nm. In embodiments, the probe light 216 may be pulsed with different intensities and time durations as needed.

Still referring to FIG. 1, the optical fiber 212 may be optically coupled to the detector 220 via the 1×2 coupler 224. Commercially available detectors may include power meters available from Newport, Thorlabs, and Ophir Photonics. The detector 220 may monitor the back reflectance of the probe light 216 directed into the photocurable material through the optical fiber 212 as the photocurable material is cured with the ultraviolet light; and determine the refractive index change of the photocurable material as the photocurable material is cured. A control unit may be communicatively coupled to the detector 220 by the coupler 224. The control unit may be utilized to determine a refractive index change of the photocurable material 204. For example, the control unit may comprise a processor and a memory storing logic, such as computer readable and executable instructions, that when executed by the processor, causes the processor to receive a detector signal, from the detector 220, indicative of the back reflectance of the probe light 216 directed into the photocurable material 204 through the optical fiber 212 as the photocurable material 204 is cured by the ultraviolet cure light 208. The control unit may also be communicatively coupled to determine a refractive index change of the photocurable material 204, as the photocurable material 204 is cured, based on the detector signal.

Still referring to FIG. 1, the ultraviolet cure light 208, which is indicated as an arrow, may be directed into the photocurable material 204. The ultraviolet cure light 208 may be emitted from an ultraviolet cure light source 228. Exemplary ultraviolet light sources may include ultraviolet LEDs, such as LED Egin products commercially available Osram Sylvania, Inc. In embodiments, the ultraviolet cure light source 228 may be communicatively coupled to the control unit, and is operable to adjust the intensity of the ultraviolet cure light 208. In embodiments, the processor may be utilized to activate the ultraviolet cure light source 228 to direct the ultraviolet cure light 208 onto the photocurable material 204.

In embodiments, the ultraviolet cure light 208 may have an intensity of from greater than or equal to 0.1 W/cm$^2$ to less than or equal to 700 W/cm$^2$ at the terminal end 212*b* of the optical fiber 212. In embodiments, the ultraviolet cure light 208 may have an intensity of from greater than or equal to 0.1 W/cm$^2$ to less than or equal to 600 W/cm$^2$, from greater than or equal to 0.1 W/cm$^2$ to less than or equal to 500 W/cm$^2$, from greater than or equal to 0.1 W/cm$^2$ to less than or equal to 400 W/cm$^2$, from greater than or equal to 0.1 W/cm$^2$ to less than or equal to 300 W/cm$^2$, from greater than or equal to 0.1 W/cm$^2$ to less than or equal to 200 W/cm$^2$, from greater than or equal to 0.1 to from less than or equal to 100, from greater than or equal to 0.1 to less than or equal to 50, from greater than or equal to 0.1 to less greater than or equal to 10, from greater than or equal to 10 W/cm$^2$ to less than or equal to 600 W/cm$^2$, from greater than or equal to 10 W/cm$^2$ to less than or equal to 500 W/cm$^2$, from greater than or equal to 10 W/cm$^2$ to less than or equal to 400 W/cm$^2$, from greater than or equal to 10 W/cm$^2$ to less than or equal to 300 W/cm$^2$, from greater than or equal to 10 W/cm$^2$ to less than or equal to 200 W/cm$^2$, from greater than or equal to 10 W/cm$^2$ to from less than or equal to 100 W/cm$^2$, from greater than or equal to 10 W/cm$^2$ to less than or equal to 50 W/cm$^2$, from greater than or equal to 50 W/cm$^2$ to less than or equal to 600 W/cm$^2$, from greater than or equal to 50 W/cm$^2$ to less than or equal to 500 W/cm$^2$, from greater than or equal to 50 W/cm$^2$ to less than or equal to 400 W/cm$^2$, from greater than or equal to 50 W/cm$^2$ to less than or equal to 300 W/cm$^2$, from greater than or equal to 50 W/cm$^2$ to less than or equal to 200 W/cm$^2$, from greater than or equal to 50 W/cm$^2$ to from less than or equal to 100 W/cm$^2$. As stated previously, the intensity of the ultraviolet cure light 208 may mimic the intensity of an ultraviolet cure light used in a manufacturing-scale draw tower for making optical fiber with a curable coating applied thereto.

Figure 3:
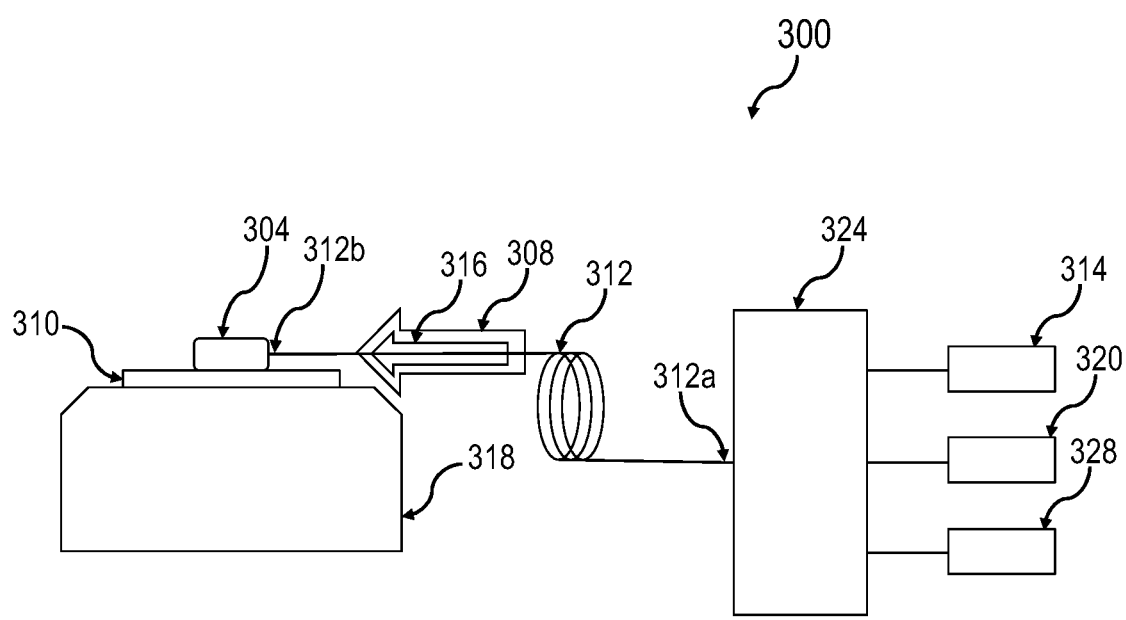
FIG. 3 schematically depicts an apparatus for monitoring the cure kinetics of a photocurable material, according to embodiments.

FIG. 3 schematically depicts an alternative embodiment of the apparatus 300 for monitoring curing of photocurable material 204. Similar to apparatus 200, the apparatus 300 for monitoring curing of photocurable material 204 may include a probe light 316 that may be delivered through an optical fiber 312. However, in this embodiment, the optical fiber 312 may be a concentric core optical fiber. As used here, "concentric core optical fiber" means an optical fiber that includes multiple cores that overlap in the sense that the cores share a common fiber axis (i.e. radial position r=0 is common to both cores) so that the cores are concentric. As used herein, a "core" may mean a region of updoped silica. In embodiments, the optical fiber 312 may be a concentric core optical fiber having two cores, where probe light is guided through one core, and cure light is guided through the other core.

The apparatus 300 for monitoring curing of photocurable material 204 may include in ultraviolet cure light 308, which may be directed into a photocurable material 304, and the ultraviolet cure light 308 may cause the photocurable material 304 to cure, as described herein with respect to the apparatus 200. In embodiments of the apparatus 300, the ultraviolet cure light 308 and the probe light 316 may both be delivered through the concentric core optical fiber 312.

Figure 4:
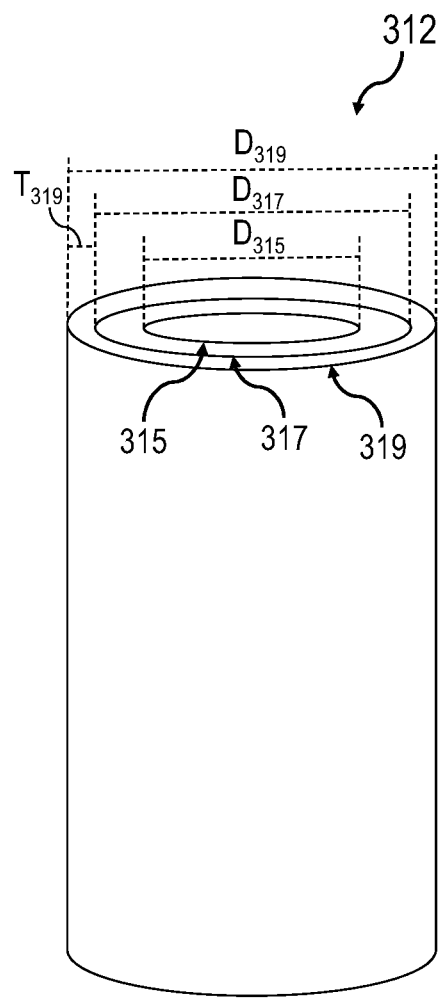
FIG. 4 schematically depicts an embodiment of a concentric core optical fiber utilized in the apparatus for monitoring the kinetics of photocurable material, according to embodiments.

Referring now to FIG. 4, an embodiment of the concentric core optical fiber 312 is schematically depicted. The concentric core optical fiber 312 may comprise a plurality of cores 315, 317 and a cladding 319 surrounding the plurality of cores 315, 317. As shown in FIG. 4, the plurality of cores 315, 317 may be concentric cores, which include an inner core 315 and an outer core 317. In embodiments, the plurality of cores 315, 317 and the cladding 319 may each comprise a glass, plastic, or other transparent material. In embodiments, the concentric core optical fiber 312 may be a multi-moded concentric core optical fiber. In embodiments, the inner core may be either a single-moded or multi-moded optical fiber. In embodiments, the outer core may be a multi-moded optical fiber.

In embodiments, utilizing the concentric core optical fiber 312 may allow for improved cure monitoring of the photocurable material when compared to apparatuses that utilize an optical fiber having a single core. For example, in embodiments, the ultraviolet cure light may be guided in the outer core 317 and the probe light may be guided in the inner core 315. Delivery of the ultraviolet cure light and the probe light through the same concentric core optical fiber 312 may allow for a simplified setup of the apparatuses for monitoring curing of photocurable material described herein. Additionally, when utilizing the concentric core optical fiber 312, the ultraviolet light 308 and the probe light 316 would not need require a separate alignment step.

Without being bound by theory, if a single-mode optical fiber includes a single core, where the ultraviolet cure light and the probe light are both contained in the single core, the ultraviolet cure light's power may be concentrated in the single core of the single-mode optical fiber. That is, the ultraviolet cure light may propagate up to 100% in the core. Meanwhile, the probe light, having a longer wavelength, for example, of 1500 nm, would propagate approximately 30% in the cladding of the single-mode optical fiber and approximately 70% in the core. As such, the ultraviolet cure light and the probe light would overlap in the single-mode, single core optical fiber. This overlap may cause monitoring errors because the ultraviolet cure light, which is curing the photocurable material, projects onto a smaller surface area (of the photocurable material) than the area being sampled by the probe light. As a result, it may be advantageous to utilize a concentric core optical fiber 312, where one of the outer core 317 or the inner core 315 guides the ultraviolet cure light 308 and the other of the outer core 317 and the inner core 315 guides the probe light 316.

Referring still to FIG. 4, the diameter of the outer core 317, $D_{317}$, may be from greater than or equal to 20 micrometers (μm) to less than or equal to 100 μm. In embodiments, $D_{317}$ may be from greater than or equal to 20 μm to less than or equal to 80 μm, from greater than or equal to 20 μm to less than or equal to 60 μm, from greater than or equal to 20 μm to less than or equal to 40 µm, from greater than or equal to 25 µm to less than or equal to 100 µm, from greater than or equal to 25 µm to less than or equal to 80 µm, from greater than or equal to 25 µm to less than or equal to 60 µm, from greater than or equal to 25 µm to less than or equal to 40 µm, from greater than or equal to 40 µm to less than or equal to 100 µm, from greater than or equal to 40 µm to less than or equal to 80 µm, from greater than or equal to 40 µm to less than or equal to 60 µm, from greater than or equal to 60 µm to less than or equal to 100 µm, from greater than or equal to 60 µm to less than or equal to 80 µm, or from greater than or equal to 80 µm to less than or equal to 100 µm. The diameter of the outer core 317 may be optimized so that the thermal effects caused by the exothermic curing reaction are negligible. In embodiments, when $D_{317}$ is from greater than or equal to 20 µm to less than or equal to 100 µm, the thermal effects caused by the exothermic curing reaction may be lessened or negligible due to faster heat dissipation.

In embodiments the diameter of the inner core 315, $D_{315}$, may be from greater than or equal to 5 micrometers (µm) to less than or equal to 10 µm. In embodiments, $D_{315}$ may be from greater than or equal to 5 µm to less than or equal to 8 µm, from greater than or equal to 5 µm to less than or equal to 6 µm, from greater than or equal to 6 µm to less than or equal to 10 µm, from greater than or equal to 6 µm to less than or equal to 8 µm, or from greater than or equal to 8 µm to less than or equal to 10 µm.

In embodiments the difference between the diameter of the outer core 317, $D_{317}$ and the diameter of the inner core 315, $D_{315}$, may be defined as the radial thickness of the outer core. In embodiments, the radial thickness of the outer core may from greater than or equal to 10 micrometers (µm) to less than or equal to 95 µm. In embodiments, $D_{315}$ may be from greater than or equal to 10 µm to less than or equal to 80 µm, from greater than or equal to 10 µm to less than or equal to 60 µm, from greater than or equal to 10 µm to less than or equal to 40 µm, from greater than or equal to 10 µm to less than or equal to 20 µm, from greater than or equal to 20 µm to less than or equal to 95 µm, from greater than or equal to 20 µm to less than or equal to 80 µm, from greater than or equal to 20 µm to less than or equal to 60 µm, or from greater than or equal to 20 µm to less than or equal to 40 µm, from greater than or equal to 40 µm to less than or equal to 95 µm, from greater than or equal to 40 µm to less than or equal to 80 µm, from greater than or equal to 40 µm to less than or equal to 60 µm, from greater than or equal to 60 µm to less than or equal to 95 µm, from greater than or equal to 60 µm to less than or equal to 80 µm, or from greater than or equal to 80 µm to less than or equal to 95 µm.

The refractive indexes for each core of the plurality of cores 315, 317 may be designed to avoid situations where the refractive index of the cores and the photocurable material are closely matched. In embodiments, the plurality of cores 315, 317 could be made with different dopants, so the value of the refractive indexes for each core of the plurality of cores 315, 317 may be different. In embodiments, the plurality of cores 315, 317 may include materials that have a higher refractive index than the materials included in the cladding 319. In embodiments, the plurality of cores 315, 317 could be made with "updopants," which are substances added to raise the refractive index of the respective core relative to pure, undoped $SiO_2$, or "downdopants" which are substances added to lower the refractive index of the respective core relative to pure, undoped $SiO_2$. Examples of updopants include $GeO_2$ (germania), $Al_2O_3$, $P_2O_5$, $TiO_2$, Cl, Br. Examples of downdopants include fluorine.

The refractive index difference between the photocurable material and each core of the plurality of cores 315, 317 may be greater than 0.002 at the wavelength of the probe light. As stated previously, the rate of polymerization of the photocurable material is dependent on temperature. That is, the refractive index of the photocurable material may have a relatively high change in refractive index as a function of the change in temperature $dn_p/dT$. For example, photocurable materials may have a $dn_p/dT$ of approximately greater than or equal to −0.001 to less than or equal to −0.0003 per degree Celsius (/° C.). Glass may have a relatively low $dn_p/dT$ of approximately greater than or equal to $1\times10^{-6}$/° C. to less than or equal to $5\times10^{-6}$1° C. In embodiments, the absolute value of the refractive index difference between the uncured photocurable material and the inner core 315, the outer core 317, or both may be at least 0.002. In embodiments, the absolute value of the refractive difference between the cured photocurable material and the inner core 315, the outer core 317, or both may be at least 0.002.

As used herein, the relative refractive index between the inner core 315 and the outer core 317 is represented by $\Delta_1$ and defined by the following equation:

$$\Delta_1 = \frac{n_{(inner\ core\ 315)} - n_{(outer\ core\ 317)}}{n_{(outer\ core\ 317)}} * 100\% \quad \text{(EQ. 4)}$$

where $n_{(inner\ core\ 315)}$ is the refractive index of the inner core 315 and $n_{(outer\ core\ 317)}$ is the refractive index of the outer core 317, and the wavelength is sodium D-line. As used herein, values of the relative refractive index are given in units of "%," unless otherwise specified. The terms: delta, $\Delta$, $\Delta$ %, % $\Delta$, delta %, and percent delta may be used interchangeably herein. In cases where the refractive index of a region is less than the average refractive index of undoped silica, the relative refractive index percent is negative and the region is referred to as a depressed index region. In cases where the refractive index of a region is greater than the average refractive index of pure silica, the relative refractive index percent of the region is positive. In embodiments, the relative refractive index ($\Delta_1$) between the inner core 315 and the outer core 317 may be from greater than or equal to 0.20% to less than or equal to 0.50%, from greater than or equal to 0.20% to less than or equal to 0.40%, from greater than or equal to 0.20% to less than or equal to 0.30%, from greater than or equal to 0.30% to less than or equal to 0.50%, from greater than or equal to 0.30% to less than or equal to 0.40%, or from greater than or equal to 0.40 to less than or equal to 0.50. In embodiments, the relative refractive index ($\Delta_1$) between the inner core 315 and the outer core 317 may be 0.33%.

As used herein, the relative refractive index between the outer core 317 and the cladding 319 is represented by 42 and defined by the following equation:

$$\Delta_2 = \frac{n_{(outer\ core\ 317)} - n_{(cladding\ 319)}}{n_{(cladding\ 319)}} * 100\% \quad \text{(EQ. 5)}$$

where $n_{(outer\ core\ 317)}$ is the refractive index of the outer core 317 and $n_{(cladding\ 319)}$ is the refractive index of the cladding 319. In embodiments, the relative refractive index (42) between the outer core 317 and the cladding 319 may be of from greater than or equal to 0.25% to less than or equal to 1.25%, from greater than or equal to 0.25% to less than or equal to 1.00%, from greater than or equal to 0.25% to less than or equal to 0.75%, from greater than or equal to 0.25% to less than or equal to 0.50%, from greater than or equal to 0.50% to less than or equal to 1.25%, from greater than or equal to 0.50% to less than or equal to 1.00%, from greater than or equal to 0.50% to less than or equal to 0.75%, from greater than or equal to 0.75% to less than or equal to 1.25%, from greater than or equal to 0.75% to less than or equal to 1.00%, or from greater than or equal to 1.00% to less than or equal to 1.25%. In embodiments, the relative refractive index (42) between the outer core 317 and the cladding 319 may be 1.00%.

Referring still to FIG. 4, the optical fiber 312 may further include a coating layer (not shown) that surrounds the cladding 319. In embodiments, the coating layer that surrounds the cladding 319 may be an acrylate polymer material. In further embodiments, the coating layer that surrounds the cladding 319 may be an acrylate polymer material that is different than the photocurable material 304.

Referring to FIG. 3 and FIG. 4, in the general operation of the apparatus 300, the probe light source 314 generates probe light 316, which is coupled into the concentric core optical fiber 312 at coupling end 312a, thereby forming a guided probe light that travels down the inner core 315 of the concentric core optical fiber 312 toward its terminal end 312b. Additionally, ultraviolet cure light source 328 generates ultraviolet cure light 308, which is coupled into the concentric core optical fiber 312 at coupling end 312a, thereby forming a guided ultraviolet cure light that travels down the outer core 317 of the concentric core optical fiber 312 toward its terminal end 312b.

With reference again to FIG. 3, the optical fiber 312, may emit a probe light 316 from a terminal end 312b of the optical fiber 312. The optical fiber 312 may be optically coupled to the probe light source 314 via a 1×2 or 1×3 or 1×n coupler 324. In embodiments, the probe light source 314 may include at least one light-emitting diode (LED) or at least one diode laser or fiber laser. In embodiments, the probe light source 314 may be a continuous wave laser. In embodiments, UV cure light source 328 may include two or more than two LEDs or lasers coupled thru coupler as needed to reach a desired brightness.

In embodiments, the probe light source 314 may emit a probe light 316 that is in the wavelength range from greater than or equal to 450 nanometers (nm) to less than or equal to 1,500 nm. In embodiments, the probe light source 314 may emit a probe light 316 that is in the wavelength range from greater than or equal to 450 nm to less than or equal to 1,000 nm, from greater than or equal to 450 nm to less than or equal to 800 nm, from greater than or equal to 450 nm to less than or equal to 600 nm, from greater than or equal to 600 nm to less than or equal to 1,000 nm, from greater than or equal to 600 nm to less than or equal to 800 nm, or from greater than or equal to 800 nm to less than or equal to 1,000 nm.

In embodiments, the probe light source 314 may emit probe light 316 that is in the visible wavelength range, for example, nominally from greater than or equal to 450 nm (blue) nm to less than or equal to 750 nm (red). In further embodiments, the probe light source 314 may emit a probe light 316 that is in the wavelength range from greater than or equal to 450 nm to less than or equal to 600 nm or from greater than or equal to 600 nm to less than or equal to 750 nm. In embodiments, the probe light 316 may be pulsed with different intensities and time durations as needed.

Still referring to FIG. 3, the optical fiber 312 may be optically coupled to the detector 320 via the coupler 324, which may be a 1×2, 1×3, or 1×n coupler. The coupler 324, may include a control unit, may be communicatively coupled to the detector 320. In embodiments, one or more additional couplers may be utilized (not shown). The detector 320 may be utilized to determine a refractive index change of the photocurable material 304. A control unit may be communicatively coupled to the detector 320 by the coupler 324. The control unit may comprise a processor and a memory storing logic, such as computer readable and executable instructions, that when executed by the processor, causes the processor to receive a detector signal, from the detector 320, indicative of the back reflectance of the probe light 316 directed into the photocurable material 304 through the optical fiber 312 as the photocurable material 304 is cured with the ultraviolet cure light 308. The control unit may also be communicatively coupled to determine a refractive index change of the photocurable material 304 as the photocurable material 304 is cured based on the detector signal.

Still referring to FIG. 3, the ultraviolet cure light 308, which is indicated as an arrow, may be directed into the photocurable material 304. The ultraviolet cure light 308 may be emitted from an ultraviolet cure light source 328. In embodiments, the ultraviolet cure light source 328 may be communicatively coupled to the control unit, and is operable to adjust the intensity of the ultraviolet cure light 308. In embodiments, the processor may be utilized to activate the ultraviolet cure light source 328 to direct the ultraviolet cure light 308 onto the photocurable material 304 through the optical fiber 312.

In embodiments, the ultraviolet cure light 308 may have an intensity of from greater than or equal to 0.1 $W/cm^2$ to less than or equal to 700 $W/cm^2$ at the terminal end 312b of the optical fiber 312. In embodiments, the ultraviolet cure light 308 may have an intensity of from greater than or equal to 0.1 $W/cm^2$ to less than or equal to 600 $W/cm^2$, from greater than or equal to 0.1 $W/cm^2$ to less than or equal to 500 $W/cm^2$, from greater than or equal to 0.1 $W/cm^2$ to less than or equal to 400 $W/cm^2$, from greater than or equal to 0.1 $W/cm^2$ to less than or equal to 300 $W/cm^2$, from greater than or equal to 0.1 $W/cm^2$ to less than or equal to 200 $W/cm^2$, from greater than or equal to 0.1 to from less than or equal to 100, from greater than or equal to 0.1 to less than or equal to 50, from greater than or equal to 0.1 to less greater than or equal to 10, from greater than or equal to 10 $W/cm^2$ to less than or equal to 600 $W/cm^2$, from greater than or equal to 10 $W/cm^2$ to less than or equal to 500 $W/cm^2$, from greater than or equal to 10 $W/cm^2$ to less than or equal to 400 $W/cm^2$, from greater than or equal to 10 $W/cm^2$ to less than or equal to 300 $W/cm^2$, from greater than or equal to 10 $W/cm^2$ to less than or equal to 200 $W/cm^2$, from greater than or equal to 10 $W/cm^2$ to from less than or equal to 100 $W/cm^2$, from greater than or equal to 10 $W/cm^2$ to less than or equal to 50 $W/cm^2$, from greater than or equal to 50 $W/cm^2$ to less than or equal to 600 $W/cm^2$, from greater than or equal to 50 $W/cm^2$ to less than or equal to 500 $W/cm^2$, from greater than or equal to 50 $W/cm^2$ to less than or equal to 400 $W/cm^2$, from greater than or equal to 50 $W/cm^2$ to less than or equal to 300 $W/cm^2$, from greater than or equal to 50 $W/cm^2$ to less than or equal to 200 $W/cm^2$, from greater than or equal to 50 $W/cm^2$ to from less than or equal to 100 $W/cm^2$. As stated previously, the intensity of the ultraviolet cure light 308 may mimic the intensity of an ultraviolet cure light used in a manufacturing-scale draw tower for making optical fiber with a curable coating applied thereto.

As stated previously, the apparatus 300 for monitoring curing of photocurable material 204 may include an ultraviolet cure light 308, which may be directed into a photocurable material 304, and the ultraviolet cure light 308 may cause the photocurable material 304 to cure. During cure, the optical fiber 312 may also be optically coupled to the detector 320 via the coupler 324. The detector 320 may be utilized to determine a refractive index change of the photocurable material 304 as the photocurable material 304 cures. The control unit, communicatively coupled to the detector 320 by the coupler 324, may comprise a processor and a memory storing logic, such as computer readable and executable instructions, that when executed by the processor, causes the processor to receive a detector signal, from the detector 320, indicative of the back reflectance of the probe light 316 directed into the photocurable material 304 through the optical fiber 312. The control unit may also be communicatively coupled to determine a refractive index change of the photocurable material 304 as the photocurable material 304 is cured based on the detector signal. As stated previously in this disclosure, the embodiments described herein may be directed to lab-scale methods of measuring the cure kinetics of photocurable materials that simulate manufacturing-scale conditions for optical fibers, such as utilizing ultraviolet light intensities greater than at least 0.1 W/cm$^2$. Even at manufacturing-scale conditions, the embodiments disclosed herein may provide data collection rate that has the ability to collect each data point in less than at least 35 milliseconds (ms).

The following examples illustrate one or more embodiments of the present disclosure as previously discussed above. The description of the embodiments is illustrative in nature and is in no way intended to be limiting it its application or use.

EXAMPLES

The embodiments described herein will be further clarified by the following examples.

Example 1

Example 1 provides compositions A-O of representative photocurable materials, which may be analyzed in accordance with the apparatuses and methods of the present disclosure. Compositions A-O are provided in more detail subsequently in Tables 1-3. The amounts of most components of each photocurable composition is expressed as weight percent (wt %). The concentration unit "pph" refers to an amount relative to a base composition that includes all monomers, oligomers, and photoinitiators. For example, for photocurable composition A, a concentration of 1.0 pph corresponds to 1 g per 100 g combined of SR601, CD9038, Photomer 3016, TPO, and Irgacure 184.

TABLE 1

Photocurable Compositions A-D.

| Component | A | B | C | D |
|---|---|---|---|---|
| SR601/Photomer4028 (wt. %) | 72 | 72 | 52 | 72 |
| CD9038 (wt. %) | 10 | 10 | 0 | 10 |
| Photomer3016 (wt. %) | 15 | 15 | 15 | 15 |
| SR602 (wt. %) | 0 | 0 | 30 | 0 |
| KWS4131 (wt. %) | 0 | 0 | 0 | 0 |
| Irgacure 184 (wt. %) | 1.5 | 1.5 | 1.5 | 1.5 |
| TPO (wt. %) | 1.5 | 1.5 | 1.5 | 1.5 |
| DC190 Fluid slip additive (pph) | 1 | 0 | 0 | 1 |
| Irganox 1035 (pph) | 1 | 0.5 | 1 | 0.5 |

SR601/Photomer 4028 is an ethoxylated(4)bisphenol A monomer available from Sartomer or IGM Resins. CD9038 is an ethoxylated(30)bisphenol A monomer available from Sartomer. Photomer 3016 is an epoxy diacrylate monomer available from IGM Resins. SR602 is an ethoxylated(10) bisphenol A monomer available from Sartomer. KWS4131 is a polyether-urethane diacrylate oligomer available from Dymax Oligomers and Coatings. IRGACURE 184 is a photoinitiator available from BASF. TPO is a photoinitiator available from BASF. DC190 is a fluid slip additive available from Dow Corning. IRGANOX 1035 is an antioxidant available from BASF.

TABLE 2

Photocurable Compositions E-L.

| Component | E | F | G | H | I | J | K | L |
|---|---|---|---|---|---|---|---|---|
| Photomer 4003 (wt. %) | 41.5 | 0 | 61.5 | 41.5 | 46.5 | 46.5 | 45.5 | 47 |
| Photomer 4960 (wt. %) | 0 | 41.5 | 0 | 0 | 0 | 0 | 0 | 0 |
| BR3741 (wt. %) | 55 | 55 | 35 | 55 | 50 | 50 | 50 | 50 |
| N-vinyl caprolactam (wt. %) | 2 | 2 | 2 | 2 | 2 | 2 | 2 | 1.5 |
| TPO (wt. %) | 1.5 | 1.5 | 1.5 | 1.5 | 1.5 | 1.5 | 2.5 | 1.5 |
| (3-acryloxypropyl)trimethoxysilane (pph) | 1 | 1 | 1 | 1 | 1 | 0.8 | 0.8 | 0.8 |
| Irganox 1035 (pph) | 1 | 1 | 1 | 1 | 1 | 1 | 1 | 1 |
| Pentaerythritol mercaptopropionate (pph) | 0.03 | 0.03 | 0.03 | 0.03 | 0.03 | 0.03 | 0.03 | 0.03 |
| Uvitex OB (pph) | 0.05 | 0 | 0 | 0 | 0 | 0 | 0 | 0 |

The cure kinetics of a sample photocurable material were monitored using apparatuses for monitoring curing according to embodiments described herein.

Example 1

Example 1 provides compositions A-O of representative photocurable materials, which may be analyzed in accordance with the apparatuses and methods of the present disclosure. Compositions A-O are provided in more detail subsequently in Tables 1-3. The amounts of most components of each photocurable composition is expressed as weight percent (wt %). The concentration unit "pph" refers Photomer 4003 is an ethoxylated nonyl phenol acrylate available from IGM Resins (now available as Photomer 4066). Photomer 4096 is a propoxylated nonyl phenol acrylate available from IGM Resins. BR3741 is an aliphatic polyether urethane acrylate oligomer available from Dymax Oligomers and Coatings. N-vinyl caprolactam is available from ISP Technologies, Inc. TPO is a photoinitiator available from BASF. IRGANOX 1035 is an antioxidant available from BASF. (3-acryloxypropyl)trimethoxysilane is an adhesion promoter available from Gelest. Pentaerythritol mercaptopropionate is available from Aldrich. UVITEX OB is an optical brightener available from BASF.

TABLE 3

Photocurable Compositions M-O.

| Component | M | N | O |
|---|---|---|---|
| CN981 (wt. %) | 40 | 0 | 0 |
| SR9020 (wt. %) | 17 | 0 | 0 |
| SR295 (wt. %) | 25 | 0 | 0 |
| SR349 (wt. %) | 15 | 0 | 0 |
| Irgacure 1850 (wt. %) | 3 | 0 | 3 |
| KWS 4131 (wt. %) | 0 | 10 | 0 |
| Photomer 3016 (wt. %) | 0 | 5 | 0 |
| Photomer 4028 (wt. %) | 0 | 82 | 87 |
| Lucirin TPO photoinitiator (wt. %) | 0 | 1.5 | 0 |
| Irgacure 184 (wt. %) | 0 | 1.5 | 0 |
| Irganox 1035 (pph) | 0 | 0.5 | 0.5 |
| BR301 (wt. %) | 0 | 0 | 10 |

CN981 is a urethane acrylate oligomer available from Sartomer Company, Inc. SR9020 is a propoxylated (3) glyceryl triacrylate monomer available from Sartomer Inc. SR295 is a pentaerythritol tetraacrylate available from Sartomer Inc. SR349 is an ethoxylated(2) bisphenol A diacrylate monomer available from Sartomer Inc. Irgacure 1850 is a hydroxycyclohexyl phenylketone and bis(2,6-dimethoxybenrzoyl)-2,4,4-trimethylpentyl phos phine oxide blend available from Ciba Specialty Chemical. KWS 4131 is a polyether urethane acrylate available from Bomar. Photomer 3016 is a bisphenol A diglycidyl diacrylate available from Cognis. Photomer 4028 is an ethoxylated (4) bisphenol A diacrylate available from Cognis. Lucirin TPO is a photoinitiator available from BASF. Irgacure 184 is a 1-hydroxycyclohexylphenyl ketone available from Ciba. Irganox 1035 is a thiodiethylene bis(3,5-di-tert-butyl-4-hydroxy)hydrocinnamate antioxidant available from Ciba Specialty Chemical. BR301 is an polyether-based urethane diacrylate oligomer available from Bomar.

Example 2

Figure 5:
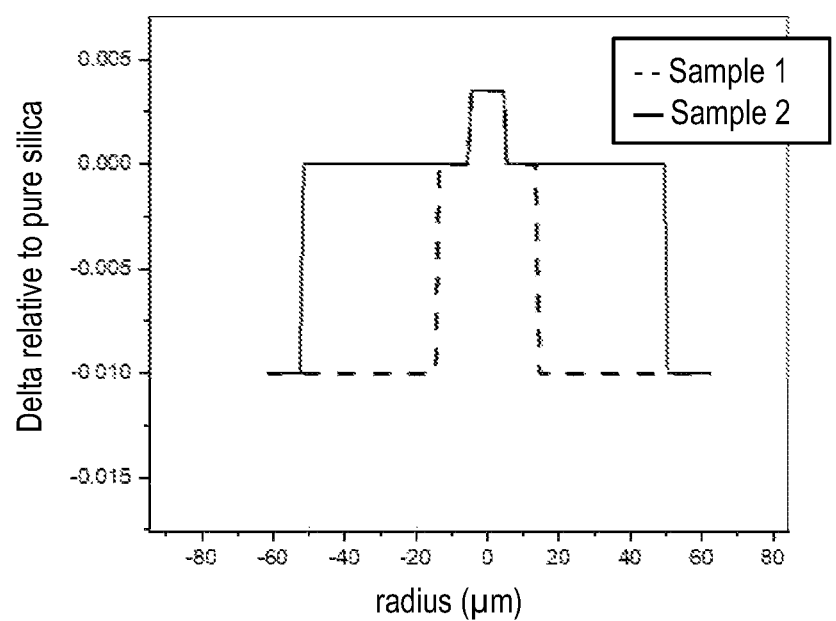
FIG. 5 graphically depicts the index profiles of an optical fiber utilized in an apparatus for monitoring the kinetics of photocurable material according to embodiments described herein.

Example 2 analyzes exemplary concentric core optical fibers, which may be utilized in accordance with the apparatuses and methods of the present disclosure. For this example, FIG. 5 illustrates the refractive index profiles of two exemplary optical fibers, Sample 1 and Sample 2, which may be utilized in embodiments of the apparatuses described herein. More specifically, FIG. 5 depicts the refractive index relative to undoped silica glass vs. the radius for two exemplary optical fibers 312 at sodium D-line wavelength. The refractive index profile is obtained by scanning a light across an end face of the fiber.

Example 3

In Example 3, a concentric core optical fiber was each placed on a glass slide and held by a fiber clip. The optical fiber utilized in Example 3 was the concentric core optical fiber of Sample 1 in FIG. 5, which was cleaved perpendicular to the central fiber axis so that it had flat ends. A 1-3 μL droplet of Photocurable Composition D was placed on the terminal end of the concentric core optical fiber. The glass slide sat on a hot stage set at 75° C. The fiber delivery included a cure light source consisting of a World Star Tech pulsed laser diode operating at a wavelength of 405 nm coupled to the concentric core optical fiber, which was coupled to a 1×3 coupler.

Figure 6:
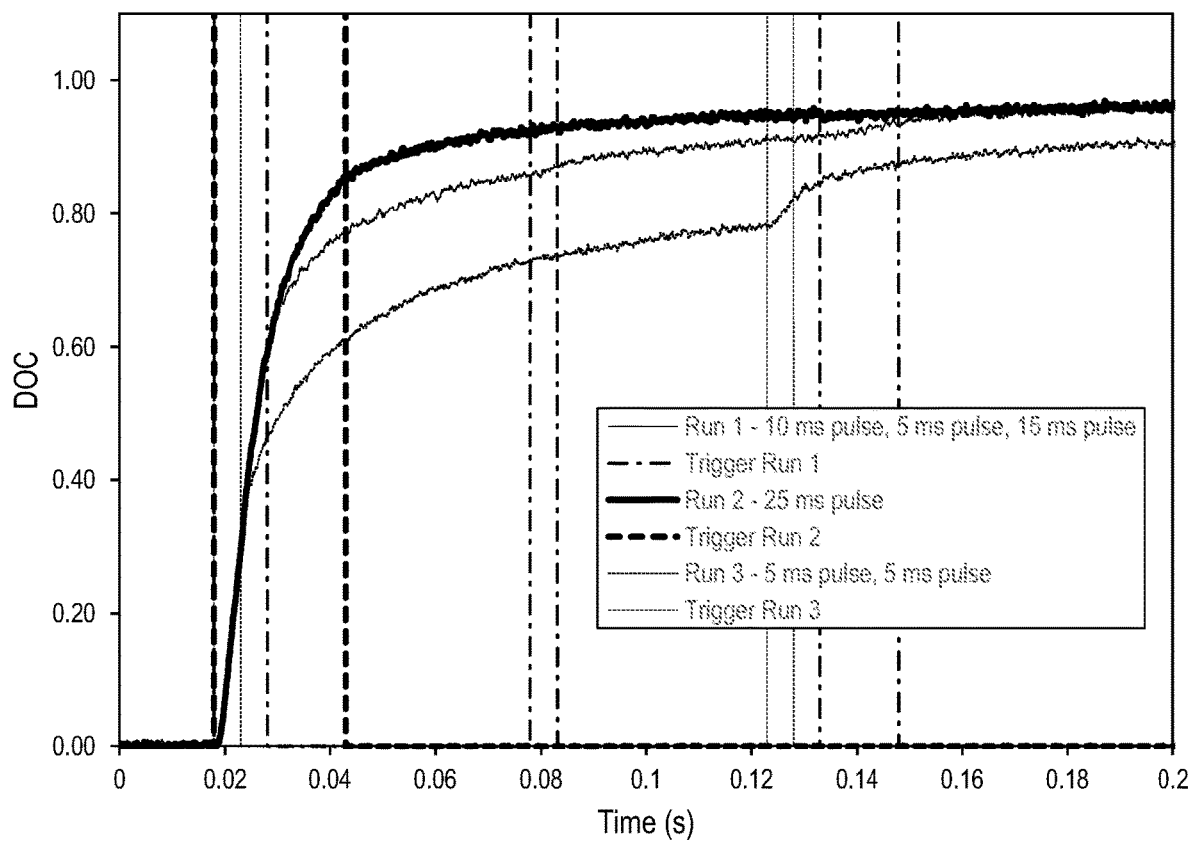
FIG. 6 graphically depicts the cure kinetics of a photocurable material measured using an apparatus for monitoring the kinetics of photocurable material according to embodiments described herein.

The power delivered from the cure light source to the terminal end of the concentric core optical fiber was 11 W/cm$^2$, and three test runs were performed. As shown in FIG. 6, in a first run, the ultraviolet cure light was pulsed at 25 ms (milliseconds). In a second run, the ultraviolet cure light was pulsed a first time at 10 ms, a second time at 5 ms, and a third time at 15 ms. In a third run, the ultraviolet cure light was pulsed twice at 5 ms. The back reflection signal was collected as a function of time throughout each run, through the coupler, which was connected to a CW MR laser at 1480 nm, which provided the probe light, and a detector that detected the back reflection signal of the probe light.

In Example 3, the refractive index of the photocurable material was then calculated based on EQ. 3 provided previously in this disclosure. $I_0$ was measured as the reflected signal in open air, assuming that the refractive index of air was 1.0 and the refractive index of the optical fiber core was 1.452 at 1480 nm. A plot of the measured results for the degree of cure (DOC) versus time is provided in FIG. 6. The results of FIG. 6 showed that the degree of cure did not appear to change when the light pulse was off, indicating negligible thermal contribution.

Additionally in Example 3, runs performed using the previously-described apparatus were compared to and comparative test runs that used FTIR methods. These results are graphically depicted in FIG. 7.

In this Example, all real-time infrared measurements were done using a Vertex 80 infrared spectrometer from Brüker Optics with an MCT detector. The interferometer was ramped to 320 kHz and spectral resolution was dropped to 16 cm to obtain one scan every 35 ms. A 1 mil (25 μm) coating film was applied to the diamond surface of a DuraSamplIR internal reflectance accessory from Smiths Detection, capped with a nitrogen purge cover, and a camera shutter/light guide assembly. UV exposure was provided using a 395 nm LED source (Lesco 395 CoolCure from American Ultraviolet) and exposure times were controlled using a Uniblitz VMM-T1 driver from Vincent Associates. Intensities were varied using a combination of distance between the light-guide and the sample, and power adjustments on the UV source. Intensities were measured with a radiometer (model ILT1400, International Light Technologies) and sensor head (model XRL340AXT, International Light Technologies). Each measurement consisted of a series of spectral scans from 4000 cm to 700 cm taken before, during, and after UV exposure. Conversion was calculated for each individual scan from the acrylate peak area (PA) centered at 1410 cm according to the following standard conversion calculation (EQ. 6):

$$\text{Conversion} = (\text{Unreacted PA} - \text{Sample PA}(X))/(\text{Unreacted PA} - \text{Full Cure PA}) \quad \text{(EQ. 6)}$$

where conversions were calculated using Array Basic programing in Grams software V9.2 (Thermo Scientific). Time files were extracted from instrument data. The experiments at different intensities from (31-231 mW/cm$^2$) were conducted by exposing the specimen for 20 s at 70° C. to ensure full degree of cure. Temperature of the DuraSamplIR surface was controlled using an Omega CN76000 monitoring system from ASI. The refractive index was measured at the D-line and was measured at the time as FTIR was completed.

Figure 7:
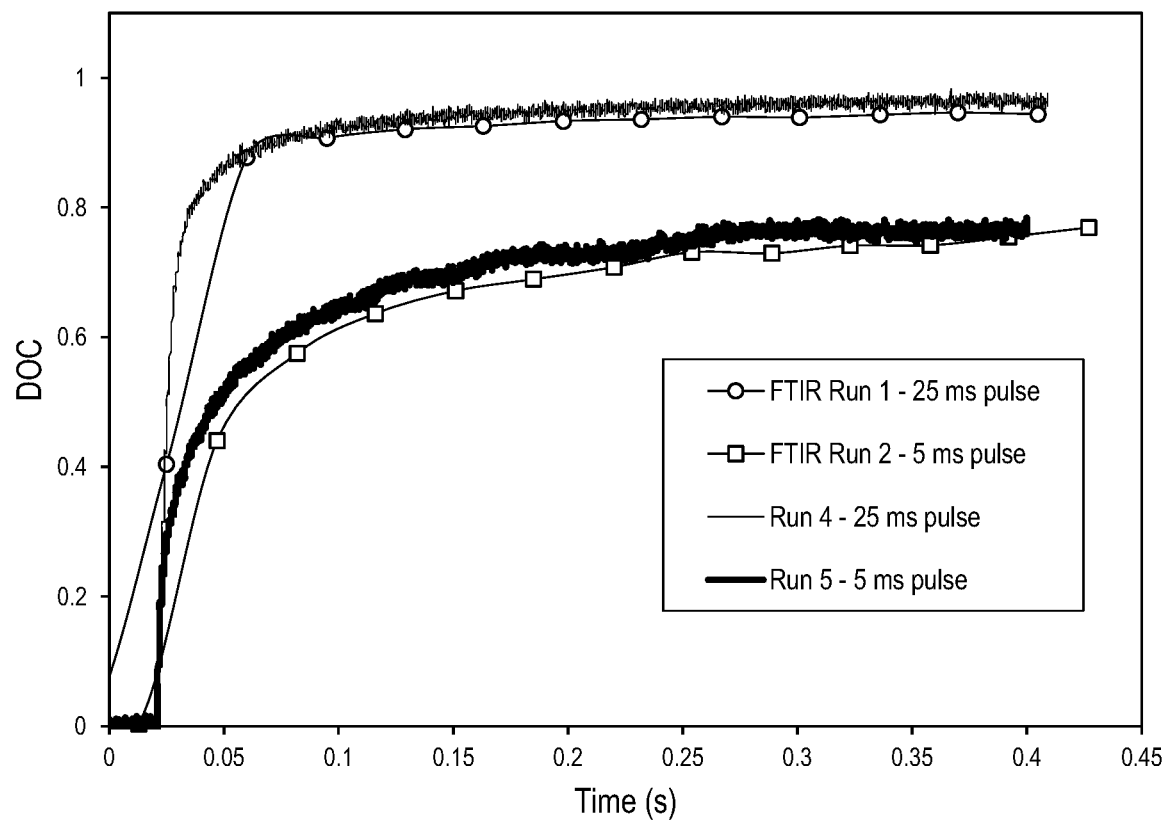
FIG. 7 graphically depicts the cure kinetics of a photocurable material as measured using FTIR methods and methods for monitoring the kinetics of photocurable material according to embodiments described herein.

In this Example, using both the FTIR method and the method described herein, one run was performed where the ultraviolet light was pulsed at 25 ms, and a second run was performed where the ultraviolet light was pulsed at 5 ms. As shown in FIG. 7, the runs performed using the presently-described methods, when compared to the runs that used the FTIR method, produced a greater amount of data points over the same time period, thus showing a faster data collection rate for the presently-disclosed methods in comparison to the FTIR methods. The greater number of data points thus provided a more accurate method for monitoring curing of die photocurable material. Therefore, the results of FIG. 7 show that the presently-disclosed apparatuses for monitoring curing of photocurable material have the ability to collect cure kinetics data for a photocurable materials under draw-like conditions, such as at manufacturing conditions, such as ultraviolet light intensities greater than at least 0.1 W/cm², coupled with a data collection rate with the ability to collect each data point in less than at least 35 ms.

It should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

What is claimed is:

1. An apparatus for monitoring curing of photocurable material, the apparatus comprising:
   an ultraviolet cure light for curing photocurable material;
   an optical fiber having a terminal end and a coupling end;
   a probe light source optically coupled to the coupling end of the optical fiber such that the optical fiber emits a probe light from the terminal end and into the photocurable material;
   a detector optically coupled to the coupling end of the optical fiber; and
   a control unit communicatively coupled to the detector, the control unit comprising:
   a processor, and
   a memory storing logic comprising computer readable and executable instructions, which, when executed by the processor, cause the processor to:
   receive a detector signal, from the detector, indicative of the back reflectance of the probe light directed into the photocurable material through the optical fiber as the photocurable material is cured with the ultraviolet cure light; and
   determine a refractive index change of the photocurable material as the photocurable material is cured based on the detector signal
   wherein
   the optical fiber is a concentric core optical fiber comprising a terminal end, a coupling end, an inner core, and an outer core in direct contact with and at least partially surrounding the inner core;
   the ultraviolet cure light is optically coupled the outer core at the coupling end of the concentric core optical fiber; and
   the probe light source is optically coupled to the inner core at the coupling end of the concentric core optical fiber.

2. The apparatus of claim 1, wherein:
   the inner core of the concentric core optical fiber comprises a first silica-based glass having a first refractive index;
   the outer core of the concentric core optical fiber comprises a second silica-based glass having a second refractive index, and
   the concentric core optical fiber further comprises a cladding in direct contact with and at least partially surrounding and the outer core.

3. The apparatus of claim 1, wherein the inner core of the concentric core optical fiber has a diameter greater than or equal to 5 micrometers (pm) to less than or equal to 8 and the outer core of the concentric core optical fiber has a diameter of from 20 μm to 100 μm.

4. The apparatus of claim 1, wherein a relative refractive index ($\Delta_1$) between the inner core and the outer core of the concentric core optical fiber is from greater than or equal to 0.20% to 0.40%.

5. The apparatus of claim 1, wherein the relative refractive index ($\Delta_2$) between the outer core and the cladding of the concentric core optical fiber is from greater than or equal to 0.75% to 1.25%.

6. A method of detecting a degree of cure of a photocurable material comprising:
   directing cure light to a photocurable material, wherein the cure light causes the photocurable material to cure;
   directing probe light to the photocurable material, the probe light interacting with the photocurable material to produce a back reflection signal, the back reflection signal comprising Fresnel reflection;
   detecting the back reflection signal;
   determining a refractive index of the photocurable material from the back reflection signal; and
   determining a degree of cure of the photocurable material from the refractive index
   wherein the cure light is directed to the photocurable material through an optical fiber, the optical fiber including a coupling end for receiving the cure light and a terminal end, the terminal end directly contacting the photocurable material, the cure light exiting the optical fiber at the terminal end, and
   wherein the probe light is directed to the photocurable material through the terminal end of the optical fiber.

7. The method of claim 6, wherein the cure light is provided by a light emitting diode (LED) or a laser diode (LD).

8. The method of claim 6, wherein the cure light is an ultraviolet cure light.

9. The method of claim 8, wherein the probe light has a wavelength longer than the cure light.

10. The method of claim 6, wherein the detecting back reflection signal comprises detecting the back reflection signal at a plurality of times spaced apart by a time interval, the time interval being less than 1 ms.

11. The method of claim 6, wherein the optical fiber includes an inner core, an outer core, and a cladding surrounding the inner core and the outer core wherein the inner core and the outer core are concentric; the outer core surrounding the inner core and having a refractive index lower than a refractive index of the inner core and greater than a refractive index of the cladding, the cure light being directed to the photocurable material through the outer core and the probe light being directed to the photocurable material through the inner core.

12. The method of claim 11, wherein the back reflection signal is directed through the optical fiber, the back reflection signal entering the optical fiber at the terminal end.

* * * * *

UNITED STATES PATENT AND TRADEMARK OFFICE
CERTIFICATE OF CORRECTION

PATENT NO. : 12,265,075 B2
APPLICATION NO. : 17/215499
DATED : April 1, 2025
INVENTOR(S) : Michael Edward DeRosa et al.

It is certified that error appears in the above-identified patent and that said Letters Patent is hereby corrected as shown below:

In the Claims

Claim 3, Column 24, Line 6, after "5 micrometers" delete "(pm)" and insert --(μm)--; and after "to 8" insert --μm--.

Signed and Sealed this
Tenth Day of February, 2026

John A. Squires
*Director of the United States Patent and Trademark Office*